United States Patent
Lee et al.

(10) Patent No.: US 6,660,854 B2
(45) Date of Patent: Dec. 9, 2003

(54) PROCESSES FOR PREPARING β-D-RIBOFURANOSE DERIVATIVES

(75) Inventors: Tai-Au Lee, Seoul (KR); Nam-Jin Park, Suwon (KR); Ja-Heouk Khoo, Kunpo (KR); Byung-Cheol Lee, Bucheon (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 10/310,887

(22) Filed: Dec. 6, 2002

(65) Prior Publication Data

US 2003/0120064 A1 Jun. 26, 2003

(30) Foreign Application Priority Data

Dec. 6, 2001 (KR) ........................................ 2001-76802

(51) Int. Cl.$^7$ .......................... C07H 19/056; C07H 5/04
(52) U.S. Cl. ................... 536/55.3; 536/28.7; 536/18.7; 536/124
(58) Field of Search ............................. 536/55.3, 18.7, 536/124, 28.7

(56) References Cited

U.S. PATENT DOCUMENTS 3,798,209 A    3/1974   Witowski et al. ........ 260/211.5

FOREIGN PATENT DOCUMENTS

JP    44080070    *  8/1974

OTHER PUBLICATIONS

Sunagawa et al. (JP 49080070). (abstract sent).*

Zhou (Zhongguo Yaowu Hauxue Zazhi (1996), 6(2), 133–135). (abstract sent).*

J.T. Witowski et al., *Journal of Medicinal Chemistry*, vol. 15, No. 11, 1972 Design, Synthesis, and Broad Spectrum Antiviral Activity of 1–β–D–Ribofuranosyl–1,2, 4–triazole–3–carboxamide and Related Nucleosides.

* cited by examiner

*Primary Examiner*—Samuel Barts
*Assistant Examiner*—Michael C. Henry
(74) *Attorney, Agent, or Firm*—Lowe, Hauptman Gilman & Berner

(57) ABSTRACT

Provided are a process for preparing β-D-ribofuranose derivatives, which are useful as an intermediate for the preparation of ribavirin. The process can be performed under a mild condition, in the presence of a catalyst selected from the group consisting of methanesulfonic acid, benzenesulfonic acid and p-toluenesulfonic acid.

13 Claims, No Drawings

PROCESSES FOR PREPARING β-D-RIBOFURANOSE DERIVATIVES

This application is based upon and claims priority from Korean Patent Application No. 10-2001-76802 filed Dec. 6, 2001, the contents of which are incorporated herein by reference.

BACKGROUND OF THE INVENTION

1. Field of the Invention

The present invention relates to a process for preparing β-D-ribofuranose derivatives, which are useful as an intermediate for the preparation of ribavirin with an antiviral activity.

2. Description of the Related Art

β-D-Ribofuranose derivatives are useful as an intermediate for the preparation of ribavirin. Processes for the preparation thereof are disclosed in U.S. Pat. No. 3,798,209 and *J. Med. Chem.*, 1972, Vol. 15, No.11, 1150~1154. The process disclosed in U.S. Pat. No. 3,798,209 may be summarized in the following reaction scheme 1:

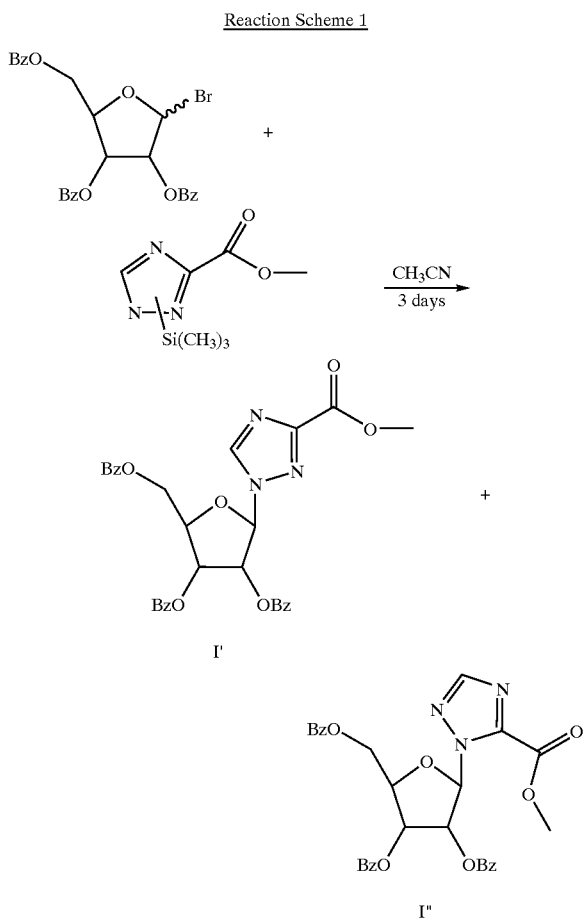

Reaction Scheme 1

In the above reaction scheme 1, Bz is a benzoyl group.

However, it takes about 3 days to complete the reaction of the above process. Further, additional isolation processes are necessary because the compounds of formula (I") are also produced as a by-product. In order to carry out the isolation processes, re-crystallization and/or column chromatography are conventionally performed, which complicates an industrial-scale mass production.

The process disclosed in *J. Med. Chem.*, 1972, Vol. 15, No. 11, 1150~1154 is illustrated in the following reaction scheme 2:

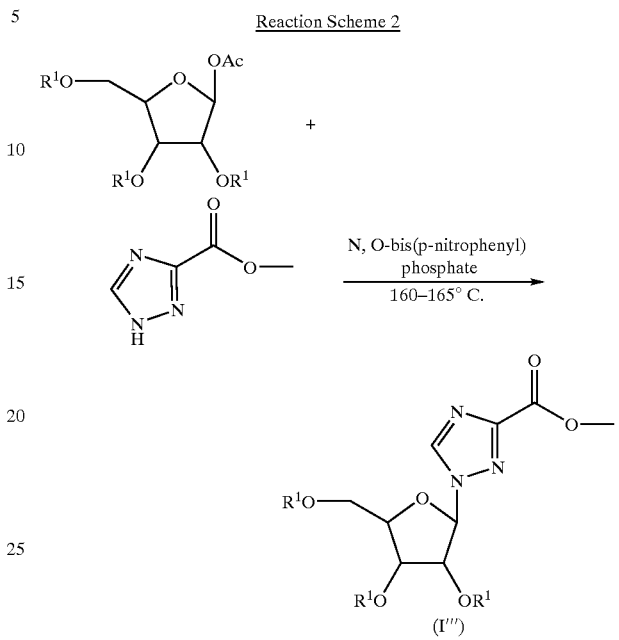

Reaction Scheme 2

In the above reaction scheme 2, Ac is an acetyl group; and $R^1$ is a protecting group for hydroxyl group.

The reaction, as shown in the scheme 2, is carried out at a high temperature, such as 160~165° C., which causes a degradation of compounds including reactants and products. Degraded compounds are changed into tar, which makes it difficult to isolate and purify an end product. The yield of the end product through the above process is relatively low, i.e., about 74~78%. There is needed an additional distillation equipment under a reduced pressure, in order to remove acetic acid that is generated during the reaction.

Further, N,O-bis(p-nitrophenyl) phosphate, used as a catalyst, is very expensive reagent, which is unfavorable for industrial-scale mass production of β-D-ribofuranose derivatives. Moreover, since the above process gives the compound of formula (I''') with gray color (i.e., low purity), an additional purification process is required in order to produce a high purity of ribavirin.

SUMMARY OF THE INVENTION

The present invention provides a process for preparing β-D-ribofuranose derivatives in high purity and yield under a mild condition, so as to be favorably applied to a large-scale mass production thereof.

In one aspect of the present invention, there is provided a process for preparing a compound of formula (I), which comprises (a) reacting a compound of formula (II) with a compound of formula (III) at 80° C.~120° C., in the presence of a catalyst selected from the group consisting of methanesulfonic acid, benzenesulfonic acid and p-toluenesulfonic acid; and (b) crystallizing the resulting compound obtained in the step (a):

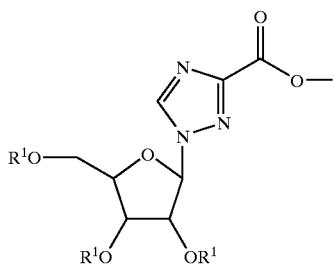

(I)

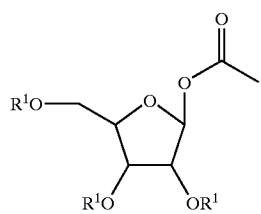

(II)

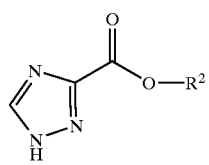

(III)

wherein, $R^1$ is a protecting group for hydroxyl group; and $R^2$ is a $C_1$–$C_4$ alkyl group.

DETAILED DESCRIPTION OF THE INVENTION

In one embodiment of the present invention, a compound of formula (II) and a compound of formula (III) are reacted under a mild condition in the presence of a catalyst and a resulting compound is crystallized, in accordance with the following reaction scheme 3 described below:

Reaction Scheme 3

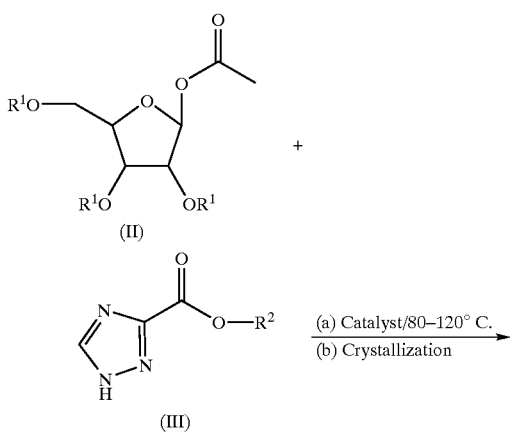

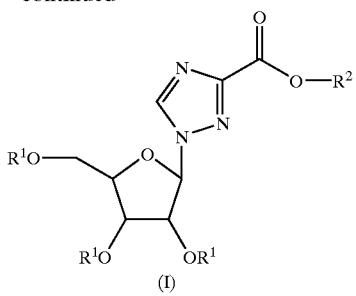

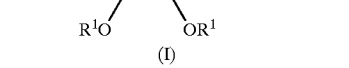

(I)

In the above reaction scheme 3, $R^1$ is a protecting group for hydroxyl group; and $R^2$ is a $C_1$–$C_4$ alkyl group.

The compounds of formula (II) and (III), which are starting materials in the process of the present invention, may be prepared by a method which is known in the art (e.g., J. Med. Chem., 1972, Vol. 15, No. 11, 1150~1154).

The protecting group for hydroxyl group includes any conventional protecting groups which are acceptable for the preparation of antiviral agents, such as acetyl group, benzoyl group and etc.

The eq. ratio of the compound of formula (II): the compound of formula (III) is preferably 1:1.0~1.2. Where eq. ratio of the compound of formula (III) to the compound of formula (II) is less than 1, the compound of formula (II) may remain un-reacted. Where the compound of formula (III) is used more than 1.2 eq. to 1 eq. of the compound of formula (II), the color of the product, i.e., the compound of formula (I), may be changed (yellow). Further, un-reacted compound of formula (III), which could remain in the reaction system, may be converted to 1,2,4-triazole-3-carboxamide during a subsequent ammonolysis for the preparation of ribavirin, which then remains as one of impurities.

In reacting the compounds of formula (II) and (III), a higher temperature raises the rate of the reaction. However, considering purity and yield of the product, the reaction is preferably performed at 80° C.~120° C., more preferably 90° C.~100° C.

The catalyst is selected from the group consisting of methanesulfonic acid, benzenesulfonic acid, and p-toluenesulfonic acid. These catalytic compounds are much cheaper than N,O-bis(p-nitrophenyl) phosphate. In addition, the catalyst allows the reaction to be carried out under a milder condition. Thus, a high reaction temperature can be avoided. Among those catalytic compounds, p-toluenesulfonic acid is preferable, in the aspect of the yield of the product.

The catalyst may be added to the reaction mixture preferably at a ratio of 0.01~0.05 eq. based on 1 eq. of the compound of formula (II), considering the yield of the product.

The reaction of the compounds of formula (II) and (III) does not require a solvent. That is, both compounds of formula (II) and (III) melt at the reaction temperature (i.e., 80° C.~120° C.) and the reaction proceeds by adding the catalyst. The reaction may be completed within preferably 3~6 hours, more preferably 4~5 hours.

In crystallizing the resulting compound, a solvent is used. The solvent for crystallization includes an alcohol, such as methanol, ethanol, butanol, isobutanol, and an aqueous solution thereof. Among them, more preferable solvent for crystallization is methanol, considering a purity of the product, a compound of formula (I).

The compound of formula (I) obtained according to the present invention can be converted to ribavirin in accordance with conventional methods disclosed in, e.g., U.S. Pat. No. 3,798,209 and *J. Med. Chem.,* 1972, Vol. 15, No. 11, 1150~1154. For example, through ammonolysis and re-crystallization, high purity ribavirin of white color can be easily obtained from the compound of formula (I) without any additional purification and/or decolorization.

The present invention is further illustrated and described by the following examples, which should not be taken to limit the scope of the invention.

EXAMPLE 1

A mixture of methyl 1,2,4-triazole-3-carboxylate (26.4 g, 0.21 mole) and β-D-ribofuranosyl-1,2,3,5-tetraacetate (60.2 g, 0.19 mole) was melted and then 1.1 g of p-toluenesulfonic acid was added thereto. The reaction mixture was reacted for 6 hours, while maintaining the temperature of the reaction mixture at 85±5° C. And then, the reaction mixture was crystallized with 300.8 ml of methanol to give 57.9 g of 1-(2,3,5-tri-O-acetyl-β-D-ribofuranosyl)-1,2,4-triazole-3-carboxylic acid methyl ester (yield: 78.9%).

NMR (CDCl$_3$) δ (ppm): 2.12 (t, 9H), 3.99 (s, 3H), 4.25 (m, 1H), 4.48 (m, 2H), 5.57 (t, 1H), 5.76 (q, 1H), 6.07 (d, 1H), 8.44 (s, 1H)

EXAMPLE 2

A mixture of methyl 1,2,4-triazole-3-carboxylate (26.4 g, 0.21 mole) and β-D-ribofuranosyl-1,2,3,5-tetraacetate (60.2 g, 0.19 mole) was melted and then 1.1 g of p-toluenesulfonic acid was added thereto. The reaction mixture was reacted for 5 hours, while maintaining the temperature of the reaction mixture at 95±5° C. And then, the reaction mixture was crystallized with 300.8 ml of methanol to give 65.9 g of 1-(2,3,5-tri-O-acetyl-β-D-ribofuranosyl)-1,2,4-triazole-3-carboxylic acid methyl ester (yield: 90%).

EXAMPLE 3

A mixture of methyl 1,2,4-triazole-3-carboxylate (26.4 g, 0.21 mole) and β-D-ribofuranosyl-1,2,3,5-tetraacetate (60.2 g, 0.19 mole) was melted and then 1.1 g of p-toluenesulfonic acid was added thereto. The reaction mixture was reacted for 3 hours, while maintaining the temperature of the reaction mixture at 105±5° C. And then, the reaction mixture was crystallized with 300.8 ml of methanol to give 58.6 g of 1-(2,3,5-tri-O-acetyl-β-D-ribofuranosyl)-1,2,4-triazole-3-carboxylic acid methyl ester (yield: 80%).

EXAMPLE 4

A mixture of methyl 1,2,4-triazole-3-carboxylate (24.0 g, 0.19 mole) and β-D-ribofuranosyl-1,2,3,5-tetraacetate (60.2 g, 0.19 mole) was melted and then 1.1 g of p-toluenesulfonic acid was added thereto. The reaction mixture was reacted for 5 hours, while maintaining the temperature of the reaction mixture at 95±5° C. And then, the reaction mixture was crystallized with 300.8 ml of methanol to give 60.0 g of 1-(2,3,5-tri-O-acetyl-β-D-ribofuranosyl)-1,2,4-triazole-3-carboxylic acid methyl ester (yield: 82%).

EXAMPLE 5

A mixture of methyl 1,2,4-triazole-3-carboxylate (28.8 g, 0.22 mole) and β-D-ribofuranosyl-1,2,3,5-tetraacetate (60.2 g, 0.19 mole) was melted and then 1.1 g of p-toluenesulfonic acid was added thereto. The reaction mixture was reacted for 5 hours, while maintaining the temperature of the reaction mixture at 95±5° C. And then, the reaction mixture was crystallized with 300.8 ml of methanol to give 66.7 g of 1-(2,3,5-tri-O-acetyl-β-D-ribofuranosyl)-1,2,4-triazole-3-carboxylic acid methyl ester (yield: 92%).

EXAMPLE 6

A mixture of methyl 1,2,4-triazole-3-carboxylate (26.4 g, 0.21 mole) and β-D-ribofuranosyl-1,2,3,5-tetraacetate (60.2 g, 0.19 mole) was melted and then 0.36 g (0.01 eq.) of p-toluenesulfonic acid was added thereto. The reaction mixture was reacted for 5 hours, while maintaining the temperature of the reaction mixture at 95±5° C. And then, the reaction mixture was crystallized with 300.8 ml of methanol to give 58.9 g of 1-(2,3,5-tri-O-acetyl-β-D-ribofuranosyl)-1,2,4-triazole-3-carboxylic acid methyl ester (yield: 81%).

EXAMPLE 7

A mixture of methyl 1,2,4-triazole-3-carboxylate (26.4 g, 0.21 mole) and β-D-ribofuranosyl-1,2,3,5-tetraacetate (60.2 g, 0.19 mole) was melted and then 1.8 g (0.05 eq.) of p-toluenesulfonic acid was added thereto. The reaction mixture was reacted for 5 hours, while maintaining the temperature of the reaction mixture at 95±5° C. And then, the reaction mixture was crystallized with 300.8 ml of methanol to give 61.7 g of 1-(2,3,5-tri-O-acetyl-β-D-ribofuranosyl)-1,2,4-triazole-3-carboxylic acid methyl ester (yield: 85%).

EXAMPLE 8

A mixture of methyl 1,2,4-triazole-3-carboxylate (26.4 g, 0.21 mole) and β-D-ribofuranosyl-1,2,3,5-tetraacetate (60.2 g, 0.19 mole) was melted and then 1.1 g of p-toluenesulfonic acid was added thereto. The reaction mixture was reacted for 5 hours, while maintaining the temperature of the reaction mixture at 95±5° C. And then, the reaction mixture was crystallized with 180.5 ml of methanol to give 68.9 g of 1-(2,3,5-tri-O-acetyl-β-D-ribofuranosyl)-1,2,4-triazole-3-carboxylic acid methyl ester (yield: 95%).

EXAMPLE 9

A mixture of methyl 1,2,4-triazole-3-carboxylate (26.4 g, 0.21 mole) and β-D-ribofuranosyl-1,2,3,5-tetraacetate (60.2 g, 0.19 mole) was melted and then 1.1 g of p-toluenesulfonic acid was added thereto. The reaction mixture was reacted for 5hours, while maintaining the temperature of the reaction mixture at 95±5° C. And then, the reaction mixture was crystallized with 421.1 ml of methanol to give 64 g of 1-(2,3,5-tri-O-acetyl-β-D-ribofuranosyl)-1,2,4-triazole-3-carboxylic acid methyl ester (yield: 88%).

EXAMPLE 10

A mixture of methyl 1,2,4-triazole-3-carboxylate (1.27 g, 0.01 mole) and 1-O-acetyl-2,3,5-tri-O-benzoyl-β-D-ribofuranose (5.04 g, 0.01 mole) was melted and then 0.095 g of p-toluenesulfonic acid was added thereto. The reaction mixture was reacted for 3 hours, while maintaining the temperature of the reaction mixture at 95±5° C. And then, the reaction mixture was crystallized with 25 ml of methanol to give 4.85 g of 1-(2,3,5-tri-O-benzoyl-β-D-ribofuranosyl)-1,2,4-triazole-3-carboxylic acid methyl ester (yield: 85%).

NMR (CDCl$_3$) δ (ppm): 3.96 (d, 3H), 4.67–4.80 (m, 2H), 4.87 (m, 1H), 6.11 (t, 1H), 6.16 (q, 1H), 6.34 (d, 1H), 7.38–8.07 (m, 15H), 8.44 (s, 1H)

EXAMPLE 11

A mixture of ethyl 1,2,4-triazole-3-carboxylate (1.41 g, 0.01 mole) and β-D-ribofuranosyl-1,2,3,5-tetraacetate (3.18 g, 0.01 mole) was melted and then 0.095 g of p-toluenesulfonic acid was added thereto. The reaction mixture was reacted for 3 hours, while maintaining the temperature of the reaction mixture at 95±5° C. And then, the reaction mixture was crystallized with 20 ml of methanol to give 3.27 g of 1-(2,3,5-tri-O-acetyl-β-D-ribofuranosyl)-1,2,4-triazole-3-carboxylic acid ethyl ester (yield: 82%).

NMR (CDCl₃) δ (ppm): 1.43 (t, 3H), 2.12 (t, 9H), 4.00 (m, 2H), 4.26 (m, 1H), 4.48 (m, 2H), 5.57 (t, 1H), 5.77 (q, 1H), 6.10 (d, 1H), 8.50 (s, 1H)

EXAMPLE 12

A mixture of methyl 1,2,4-triazole-3-carboxylate (1.27 g, 0.01 mole) and β-D-ribofuranosyl-1,2,3,5-tetraacetate (3.18 g, 0.01 mole) was melted and then 0.048 g of methanesulfonic acid was added thereto. The reaction mixture was reacted for 5 hours, while maintaining the temperature of the reaction mixture at 95±5° C. And then, the reaction mixture was crystallized with 300.8 ml of methanol to give 3.0 g of 1-(2,3,5-tri-O-acetyl-β-D-ribofuranosyl)-1,2,4-triazole-3-carboxylic acid methyl ester (yield: 79%).

EXAMPLE 13

A mixture of methyl 1,2,4-triazole-3-carboxylate (1.27 g, 0.01 mole) and β-D-ribofuranosyl-1,2,3,5-tetraacetate (3.18 g, 0.01 mole) was melted and then 0.079 g of benzenesulfonic acid was added thereto. The reaction mixture was reacted for 5 hours, while maintaining the temperature of the reaction mixture at 95±5° C. And then, the reaction mixture was crystallized with 300.8 ml of methanol to give 3.08 g of 1-(2,3,5-tri-O-acetyl-β-D-ribofuranosyl)-1,2,4-triazole-3-carboxylic acid methyl ester (yield: 80%).

EXAMPLE 14

A mixture of methyl 1,2,4-triazole-3-carboxylate (1.27 g, 0.01 mole) and β-D-ribofuranosyl-1,2,3,5-tetraacetate (3.18 g, 0.01 mole) was melted and then 0.076 g of p-toluenesulfonic acid was added thereto. The reaction mixture was reacted for 3 hours, while maintaining the temperature of the reaction mixture at 95±5° C. And then, the reaction mixture was crystallized with 20 ml of ethanol to give 2.92 g of 1-(2,3,5-tri-O-acetyl-β-D-ribofuranosyl)-1,2,4-triazole-3-carboxylic acid methyl ester (yield: 92%).

EXAMPLE 15

A mixture of methyl 1,2,4-triazole-3-carboxylate (1.27 g, 0.01 mole) and β-D-ribofuranosyl-1,2,3,5-tetraacetate (3.18 g, 0.01 mole) was melted and then 0.076 g of p-toluenesulfonic acid was added thereto. The reaction mixture was reacted for 3 hours, while maintaining the temperature of the reaction mixture at 95±5° C. And then, the reaction mixture was crystallized with 20 ml of butanol to give 2.70 g of 1-(2,3,5-tri-O-acetyl-β-D-ribofuranosyl)-1,2,4-triazole-3-carboxylic acid methyl ester (yield: 85%).

EXAMPLE 16

A mixture of methyl 1,2,4-triazole-3-carboxylate (1.27 g, 0.01 mole) and β-D-ribofuranosyl-1,2,3,5-tetraacetate (3.18 g, 0.01 mole) was melted and then 0.076 g of p-toluenesulfonic acid was added thereto. The reaction mixture was reacted for 3 hours, while maintaining the temperature of the reaction mixture at 95±5° C. And then, the reaction mixture was crystallized with 20 ml of isobutanol to give 2.92 g of 1-(2,3,5-tri-O-acetyl-β-D-ribofuranosyl)-1,2,4-triazole-3-carboxylic acid methyl ester (yield: 92%).

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A process for preparing a β-D-ribofuranose compound of formula (I), which comprises the steps of:
   (a) reacting a compound of formula (II) with a compound of formula (III) at about 90° C. to 100° C., in the presence of a catalyst selected from the group consisting of methanesulfonic acid, benzenesulfonic acid and p-toluenesulfonic acid; and
   (b) crystallizing the resulting compound obtained in step (a):

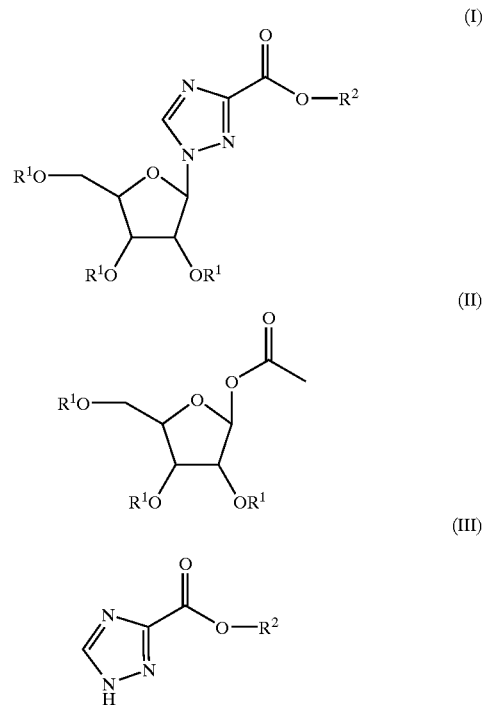

wherein R¹ is a protecting group for hydroxyl group; and R² is a C₁–C₄ alkyl group.

2. The process of claim 1, wherein the catalyst is p-toluenesulfonic acid.

3. The process of claim 1, wherein the amount of the catalyst is about 0.01 to 0.05 eq. to 1 eq. of the compound of formula (II).

4. The process of claim 1, wherein the eq. ratio of the compound of formula (II):the compound of formula (III) is about 1:1.0 to 1.2.

5. The process of claim 1, wherein the reaction time of step (a) is about 3 to 6 hours.

6. The process of claim 1, wherein the reaction of step (a) is carried out in the absence of a solvent.

7. The process of claim 1, wherein a solvent for crystallization in step (b) is an alcohol.

8. The process of claim 7, wherein the solvent for crystallization is selected from the group consisting of methanol, ethanol, butanol, isobutanol, and aqueous solutions thereof.

9. The process of claim 8, wherein the solvent for crystallization is methanol.

10. The process of claim 1, wherein R¹ is acetyl or benzoyl group.

11. The process of claim 1, wherein the compound of the formula (I) is 1-(2,3,5-tri-O-acetyl-β-D-ribofuranosyl)-1,2,4-triazole-3-carboxylic acid methyl ester.

12. A process for producing ribavirin having a white color, which comprises the steps of:
 (a) preparing a β-D-ribofuranose compound of the formula (I) of claim 1, and
 (b) subjecting the compound of the formula (I) to ammonolysis and recrystallization.

13. The process of claim 12, which is conducted without any additional purification or decolorization step or both.

* * * * *